(12) United States Patent
Mishra

(10) Patent No.: US 9,050,466 B2
(45) Date of Patent: Jun. 9, 2015

(54) FULLY IMPLANTABLE COCHLEAR IMPLANT SYSTEMS INCLUDING OPTIONAL EXTERNAL COMPONENTS AND METHODS FOR USING THE SAME

(71) Applicant: Advanced Bionics AG, Staefa (CH)

(72) Inventor: Lakshmi N. Mishra, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/214,078

(22) Filed: Mar. 14, 2014

(65) Prior Publication Data

US 2014/0200630 A1    Jul. 17, 2014

Related U.S. Application Data

(62) Division of application No. 12/910,389, filed on Oct. 22, 2010, now Pat. No. 8,706,246.

(60) Provisional application No. 61/254,295, filed on Oct. 23, 2009.

(51) Int. Cl.
*A61N 1/05*    (2006.01)
*A61N 1/36*    (2006.01)

(52) U.S. Cl.
CPC ........... *A61N 1/36032* (2013.01); *A61N 1/0541* (2013.01)

(58) Field of Classification Search
None
See application file for complete search history.

(56) References Cited

U.S. PATENT DOCUMENTS

| | | | |
|---|---|---|---|
| 5,938,691 | A  | 8/1999  | Schulman et al. |
| 2005/0256651 | A1 | 11/2005 | Taylor |
| 2006/0029248 | A1 | 2/2006  | Waldron et al. |
| 2008/0085023 | A1 | 4/2008  | Kulkarni et al. |
| 2008/0147144 | A1 | 6/2008  | Money et al. |

FOREIGN PATENT DOCUMENTS

WO    WO-96/25832    8/1996

OTHER PUBLICATIONS

International Search Report and Written Opinion received in International Application No. PCT/US2010/053834.
Non-Final Office Action received in U.S. Appl. No. 12/910,389, dated Mar. 7, 2013.
Final Office Action received in U.S. Appl. No. 12/910,389, dated Jul. 2, 2013.

*Primary Examiner* — Brian T Gedeon
*Assistant Examiner* — Ankit Tejani
(74) *Attorney, Agent, or Firm* — ALG Intellectual Property, LLC

(57) ABSTRACT

An exemplary method includes 1) detecting, by an external module configured to be positioned external to and worn by a patient, an input audio signal presented to the patient, 2) acoustically transmitting, by the external module, an audio signal representative of the input audio signal, 3) detecting, by an implantable module configured to be implanted within the patient, the acoustically transmitted audio signal, 4) generating, by the implantable module, one or more stimulation parameters based on the acoustically transmitted audio signal, and 5) applying, by the implantable module, electrical stimulation representative of the input audio signal to one or more stimulation sites within the patient in accordance with the one or more stimulation parameters.

10 Claims, 12 Drawing Sheets

FULLY IMPLANTABLE COCHLEAR IMPLANT SYSTEMS INCLUDING OPTIONAL EXTERNAL COMPONENTS AND METHODS FOR USING THE SAME

RELATED APPLICATIONS

The present application is a divisional application of U.S. patent application Ser. No. 12/910,389, filed Oct. 22, 2010, which claims priority under 35 U.S.C. §119(e) to U.S. Provisional Patent Application No. 61/254,295 by Lakshmi N. Mishra, filed on Oct. 23, 2009. The contents of both applications are hereby incorporated by reference in their entirety.

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea. The electrodes form a number of stimulation channels through which electrical stimulation pulses may be applied directly to auditory nerves within the cochlea. An audio signal may then be presented to a patient by translating the audio signal into a number of electrical stimulation pulses and applying the stimulation pulses directly to the auditory nerve within the cochlea via one or more of the electrodes.

Conventional cochlear implant systems include external components that are worn on the head and/or ear of a patient. The external components typically include a microphone for detecting sounds in the patient's environment, audio processing circuitry for modifying, digitizing, and/or amplifying the detected sounds, and a transmitter for sending radio frequency signals representative of the detected sounds to an implanted cochlear stimulator. Such external components are often relatively large, cumbersome, and noticeable by others.

Hence, many patients would prefer a fully implantable cochlear implant system that does not include unsightly external components. However, fully implantable cochlear systems have certain limitations. For example, a microphone implanted beneath a patient's skin may detect bodily noises (e.g., the patient's heartbeat) that may interfere with the quality of the patient's listening experience. Additionally, components within a fully implantable cochlear implant system may become degraded or damaged during use. Oftentimes, surgery may be required to properly repair and/or upgrade such components. Accordingly, a patient may desire the capability to optionally use external components in conjunction with a fully implantable cochlear implant system to compensate for and/or to enhance the performance of the implanted components.

SUMMARY

An exemplary cochlear implant system includes an external module configured to be positioned external to and worn by a patient, the external module having an external microphone configured to detect an input audio signal presented to the patient, and an external speaker configured to acoustically transmit an audio signal representative of the input audio signal. The exemplary cochlear implant system further includes an implantable module configured to be implanted within the patient, the implantable module having an internal microphone configured to detect the acoustically transmitted audio signal, an internal sound processor configured to generate one or more stimulation parameters based on the acoustically transmitted audio signal, and an internal cochlear stimulator configured to apply electrical stimulation representative of the input audio signal to one or more stimulation sites within the patient in accordance with the one or more stimulation parameters.

An exemplary method includes detecting, by an external module configured to be positioned external to and worn by a patient, an input audio signal presented to the patient, acoustically transmitting, by the external module, an audio signal representative of the input audio signal, detecting, by an implantable module configured to be implanted within the patient, the acoustically transmitted audio signal, generating, by the implantable module, one or more stimulation parameters based on the acoustically transmitted audio signal, and applying, by the implantable module, electrical stimulation representative of the input audio signal to one or more stimulation sites within the patient in accordance with the one or more stimulation parameters.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
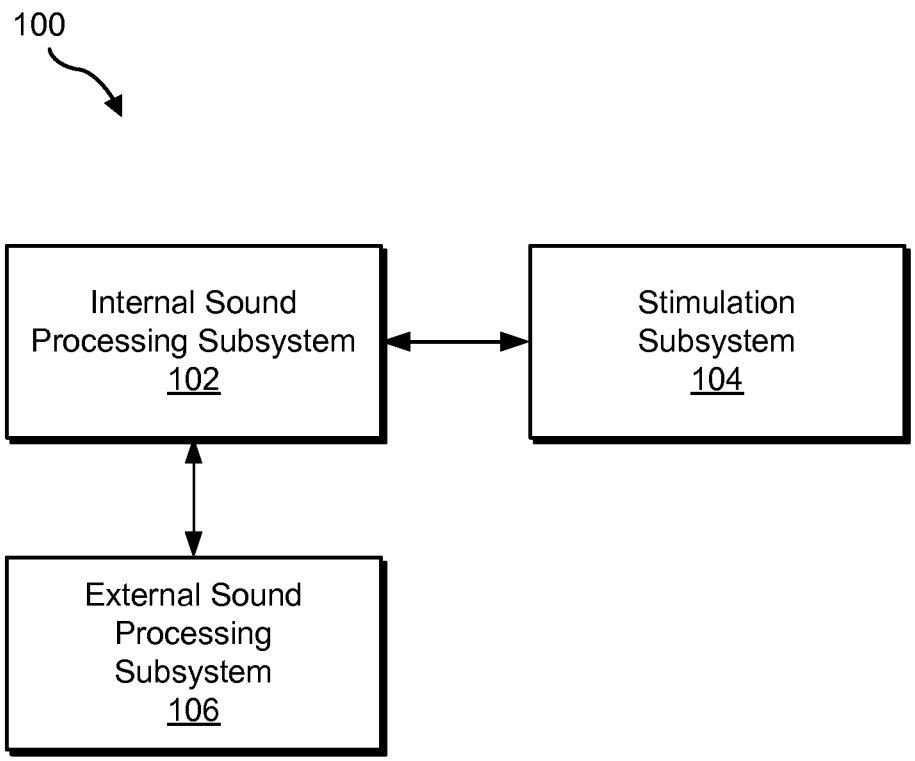
FIG. 1 illustrates an exemplary cochlear implant system according to principles described herein.

Fully implantable cochlear implant systems including optional external components and methods for using the cochlear implant systems are described herein. In some examples, a cochlear implant system may include an external module configured to be positioned external to and worn by a patient. The external module may include, e.g., an external microphone configured to detect an input audio signal presented to the patient and an external speaker configured to acoustically transmit an audio signal representative of the input audio signal. The cochlear implant system may also include an implantable module configured to be implanted within the patient. The implantable module may include, e.g., an internal microphone configured to detect the acoustically transmitted audio signal, an internal sound processor configured to generate one or more stimulation parameters based on the acoustically transmitted audio signal, and an internal cochlear stimulator configured to apply electrical stimulation representative of the input audio signal to one or more stimulation sites within the patient in accordance with the one or more stimulation parameters.

The cochlear implant systems and methods described herein may result in an enhanced listening experience for the cochlear implant patient and may provide the patient with an option of selectively utilizing external components in conjunction with fully implantable components. The cochlear implant systems and methods described herein may enable a cochlear implant patient to receive stimulation representing various sounds in the patient's environment using a fully implantable system alone. The cochlear implant systems and methods may also enable the patient to utilize external components (e.g., an externally worn headpiece) to enhance the quality of sounds detected by an implanted microphone and/or to compensate for various implanted components that are not functioning properly. Various heuristics applied to an audio signal detected by an implanted microphone may filter noise in the audio signal, such as bodily noise, that may interfere with the patient's listening experience.

A minimal number of components may be required to transmit an audio signal from an external module to an implanted module of a cochlear implant system described herein. For example, the external module may acoustically transmit an audio signal from an external speaker to an implanted microphone of the implanted module. The implanted microphone may be utilized to detect audio signals in the patient's external environment as well as audio signals transmitted from an external module. Therefore, additional components do not need to be installed on the implanted module to provide a communication path between the external module and the implanted module. Accordingly, external components may be readily utilized in conjunction with a fully implantable system without requiring a significant amount of additional space and without requiring the addition of excess and/or redundant components.

FIG. 1 illustrates an exemplary cochlear implant system 100. As shown in FIG. 1, cochlear implant system 100 may include an internal sound processing subsystem 102 and a stimulation subsystem 104 configured to communicate with one another. Cochlear implant system 100 may also include an external sound processing subsystem 106 selectively and communicatively coupled to internal sound processing subsystem 102.

Internal sound processing subsystem 102 may be configured to detect or sense an audio signal and divide the audio signal into a plurality of analysis channels each containing a frequency domain signal (or simply "signal") representative of a distinct frequency portion of the audio signal. Internal sound processing subsystem 102 may the generate one or more stimulation parameters based on the frequency domain signals and direct stimulation subsystem 104 to generate and apply electrical stimulation to one or more stimulation sites in accordance with the one or more stimulation parameters. The stimulation parameters may control various parameters of the electrical stimulation applied to a stimulation site by stimulation subsystem 104 including, but not limited to, a stimulation configuration, a frequency, a pulse width, an amplitude, a waveform (e.g., square or sinusoidal), an electrode polarity (i.e., anode-cathode assignment), a location (i.e., which electrode pair or electrode group receives the stimulation current), a burst pattern (e.g., burst on time and burst off time), a duty cycle or burst repeat interval, a spectral tilt, a ramp on time, and a ramp off time of the stimulation current that is applied to the stimulation site.

Figure 2:
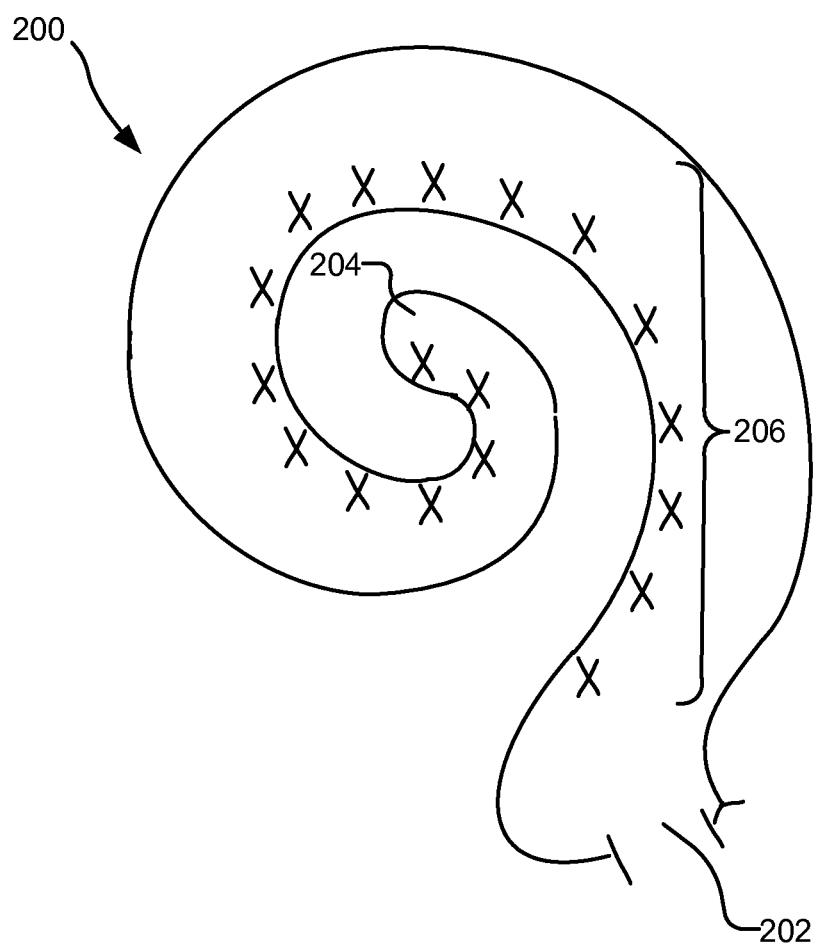
FIG. 2 illustrates a schematic structure of the human cochlea according to principles described herein.

Stimulation subsystem 104 may be configured to generate and apply electrical stimulation (also referred to herein as "stimulation current" and/or "stimulation pulses") to one or more stimulation sites within the cochlea of a patient in accordance with the one or more stimulation parameters transmitted thereto by internal sound processing subsystem 102. The one or more stimulation sites to which electrical stimulation is applied may include any target area or location within the cochlea. FIG. 2 illustrates a schematic structure of the human cochlea 200. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 104 may therefore be configured to apply electrical stimulation to different locations within the cochlea 200 (e.g., different locations along the auditory nerve tissue 206) to provide a sensation of hearing.

Returning to FIG. 1, internal sound processing subsystem 102 and stimulation subsystem 104 may be configured to operate in accordance with one or more control parameters. These control parameters may be configured to specify one or more stimulation parameters, operating parameters, and/or any other parameters as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

External sound processing subsystem 106 may be optionally utilized by a cochlear implant patient in conjunction with internal sound processing subsystem 102 and stimulation subsystem 104. External sound processing subsystem 106 may be configured to detect or sense an input audio signal and acoustically transmit an audio signal representative of the input audio signal to internal sound processing subsystem 102. Internal sound processing subsystem 102 may then generate the one or more stimulation parameters in accordance with the acoustically transmitted audio signal.

In some examples, external sound processing subsystem 106 may be configured to process the input audio signal prior to transmitting the audio signal to the internal sound processing subsystem 102. For example, as will be described in more detail below, external sound processing subsystem 106 may be configured to transpose and/or amplify the input audio signal prior to transmitting the audio signal to the internal sound processing subsystem 102.

Cochlear implant system 100, including internal sound processing subsystem 102, stimulation subsystem 104, and/or external sound processing subsystem 106 may include any hardware, computer-implemented instructions (e.g., software), firmware, or combinations thereof configured to perform one or more of the processes described herein. For example, cochlear implant system 100, including internal sound processing subsystem 102, stimulation subsystem 104, and external sound processing subsystem 106 may include hardware (e.g., one or more signal processors and/or other computing devices) configured to perform one or more of the processes described herein.

One or more of the processes described herein may be implemented at least in part as instructions executable by one or more computing devices. In general, a processor receives instructions from a computer-readable medium (e.g., a memory, etc.) and executes those instructions, thereby performing one or more processes, including one or more of the processes described herein. Such instructions may be stored and/or transmitted using any of a variety of known computer-readable media.

A computer-readable medium (also referred to as a processor-readable medium) includes any medium that participates in providing data (e.g., instructions) that may be read by a computing device (e.g., by a processor within internal sound processing subsystem 102). Such a medium may take many forms, including, but not limited to, non-volatile media and/or volatile media. Exemplary computer-readable media that may be used in accordance with the systems and methods described herein include, but are not limited to, random access memory ("RAM"), dynamic RAM, a PROM, an EPROM, a FLASH-EEPROM, any other memory chip or cartridge, or any other medium from which a computing device can read.

Figure 3:
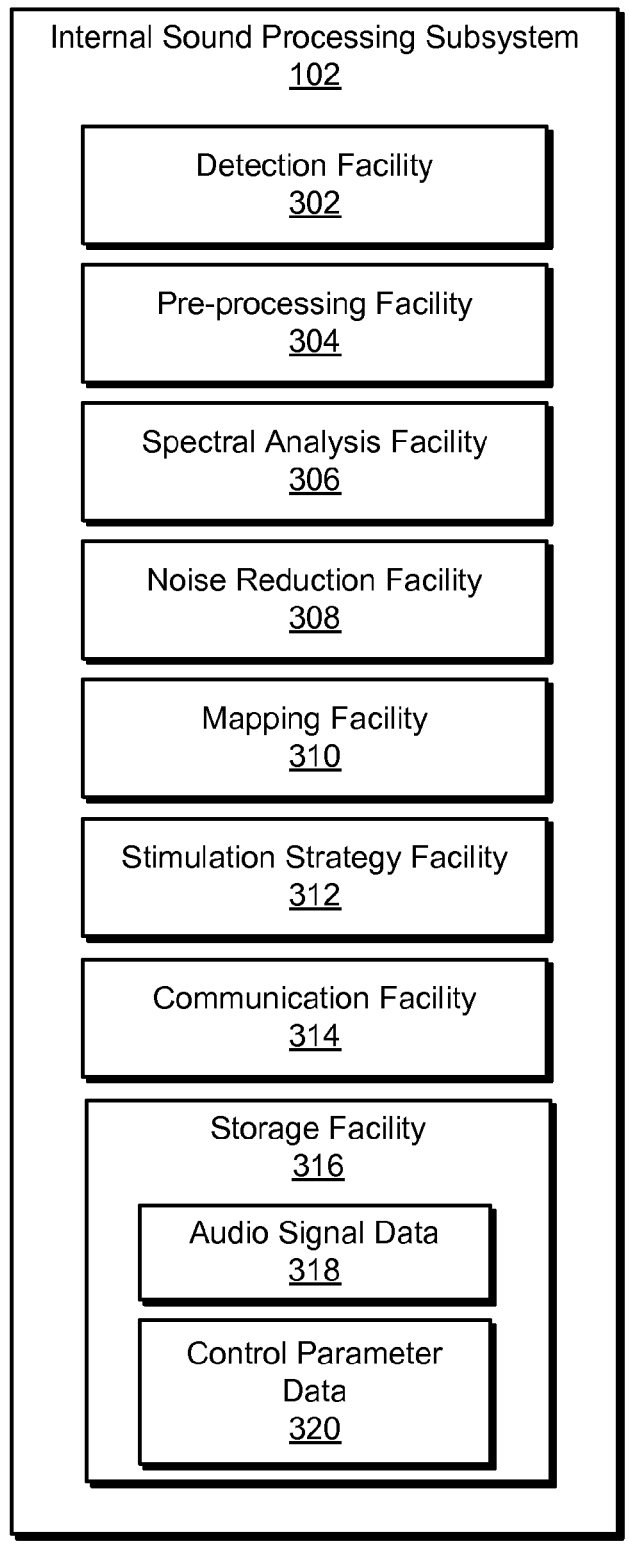
FIG. 3 illustrates exemplary components of an internal sound processing subsystem according to principles described herein.

FIG. 3 illustrates exemplary components of internal sound processing subsystem 102. As shown in FIG. 3, internal sound processing subsystem 102 may include a detection facility 302, a pre-processing facility 304, a spectral analysis facility 306, a noise reduction facility 308, a mapping facility 310, a stimulation strategy facility 312, a communication facility 314, and a storage facility 316, which may be in communication with one another using any suitable communication technologies. Each of these facilities 302-316 may include any combination of hardware, software, and/or firmware as may serve a particular application. For example, one or more of facilities 302-316 may include a computing device or processor configured to perform one or more of the functions described herein. Facilities 302-316 will now be described in more detail.

Detection facility 302 may be configured to detect or sense one or more audio signals and convert the detected signals to corresponding electrical signals. To this end, detection facility 302 may include a microphone or other transducer. The one or more audio signals may include speech, music, ambient noise, bodily noise, and/or other sounds. In some examples, the one or more audio signals may include an audio signal acoustically transmitted by external sound processing subsystem 106, as will be described in greater detail below.

Pre-processing facility 304 may be configured to perform various signal processing operations on the one or more audio signals detected by detection facility 302. For example, pre-processing facility 304 may amplify a detected audio signal, convert the audio signal to a digital signal, filter the digital signal with a pre-emphasis filter, subject the digital signal to automatic gain control, and/or perform one or more other signal processing operations on the detected audio signal.

Spectral analysis facility 306 may be configured to divide the audio signal into a plurality of analysis channels each containing a frequency domain signal representative of a distinct frequency portion of the audio signal. For example, spectral analysis facility 306 may include a plurality of bandpass filters configured to divide the audio signal into a plurality of frequency channels or bands. Additionally or alternatively, spectral analysis facility 306 may be configured to convert the audio signal from a time domain into a frequency domain and then divide the resulting frequency bins into the plurality of analysis channels. To this end, spectral analysis facility 306 may include one or more components configured to apply a Discrete Fourier Transform (e.g., a Fast Fourier Transform ("FFT")) to the audio signal.

Spectral analysis facility 306 may be configured to divide the audio signal into any number of analysis channels as may serve a particular application. In some examples, the total number of analysis channels is set to be less than or equal to a total number of stimulation channels through which electrical stimulation representative of the audio signal is applied to a cochlear implant patient.

Noise reduction facility 308 may be configured to filter out portions of the audio signal in accordance with any suitable filtering and/or noise reduction heuristic as may serve a particular application. For example, as will be described in more detail below, noise reduction facility 308 may be configured to filter out acoustic content within the audio signal in accordance with one or more filtering parameters. In some examples, noise reduction facility 308 may be configured to at least partially remove undesired audio content from one or more of the analysis channels, such as bodily noises picked up by an internally implanted microphone.

Mapping facility 310 may be configured to map the signals within the analysis channels to electrical stimulation pulses to be applied to a patient via one or more stimulation channels. For example, signal levels of the signals within the analysis channels are mapped to amplitude values used to define electrical stimulation pulses that are applied to the patient by stimulation subsystem 104 via one or more corresponding stimulation channels. Mapping facility 310 may be further configured to perform additional processing of the signals contained within the analysis channels, such as signal compression.

Stimulation strategy facility 312 may be configured to generate one or more stimulation parameters based on the noise reduced signals within the analysis channels and in accordance with one or more stimulation strategies. Exemplary stimulation strategies include, but are not limited to, a current steering stimulation strategy and an N-of-M stimulation strategy.

Communication facility 314 may be configured to facilitate communication between internal sound processing subsystem 102 and stimulation subsystem 104. For example, communication facility 314 may include one or more wires or the like that are configured to facilitate direct communication with stimulation subsystem 104.

Storage facility 316 may be configured to maintain audio signal data 318 representative of an audio signal detected by detection facility 302 and control parameter data 320 representative of one or more control parameters, which may include one or more stimulation parameters to be transmitted from internal sound processing subsystem 102 to stimulation subsystem 104. Storage facility 316 may be configured to maintain additional or alternative data as may serve a particular application.

Figure 4:
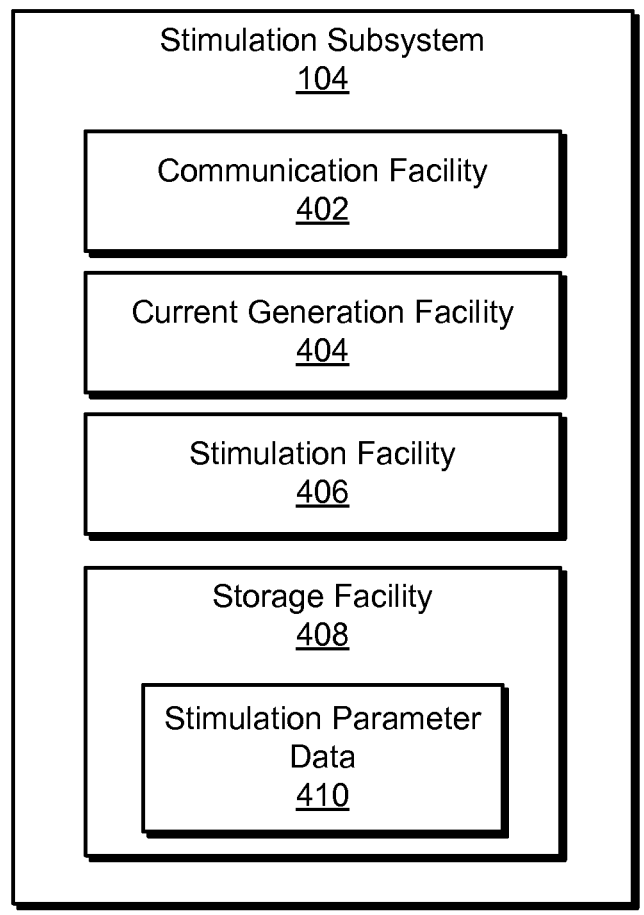
FIG. 4 illustrates exemplary components of a stimulation subsystem according to principles described herein.

FIG. 4 illustrates exemplary components of stimulation subsystem 104. As shown in FIG. 4, stimulation subsystem 104 may include a communication facility 402, a current generation facility 404, a stimulation facility 406, and a storage facility 408, which may be in communication with one another using any suitable communication technologies. Each of these facilities 402-408 may include any combination of hardware, software, and/or firmware as may serve a particular application. For example, one or more of facilities 402-408 may include a computing device or processor configured to perform one or more of the functions described herein. Facilities 402-408 will now be described in more detail.

Communication facility 402 may be configured to facilitate communication between stimulation subsystem 104 and internal sound processing subsystem 102. For example, communication facility 402 may be configured to transmit one or more status signals and/or other data to internal sound processing subsystem 102.

Current generation facility 404 may be configured to generate electrical stimulation in accordance with one or more control parameters, such as stimulation parameters received from internal sound processing subsystem 102. To this end, current generation facility 404 may include one or more current generators and/or any other circuitry configured to facilitate generation of electrical stimulation.

Stimulation facility 406 may be configured to apply the electrical stimulation generated by current generation facility 404 to one or more stimulation sites within the cochlea of a patient in accordance with the one or more stimulation strategies selected by stimulation strategy facility 314. To this end, as will be illustrated in more detail below, stimulation facility 406 may include one or more electrodes disposed on a lead that may be inserted within the cochlea.

Storage facility 408 may be configured to maintain stimulation parameter data 410 as received from internal sound processing subsystem 102. Stimulation parameter data 410 may be representative of one or more stimulation parameters configured to define the electrical stimulation generated and applied by stimulation subsystem 104. Storage facility 408 may be configured to maintain additional or alternative data as may serve a particular application.

Figure 5:
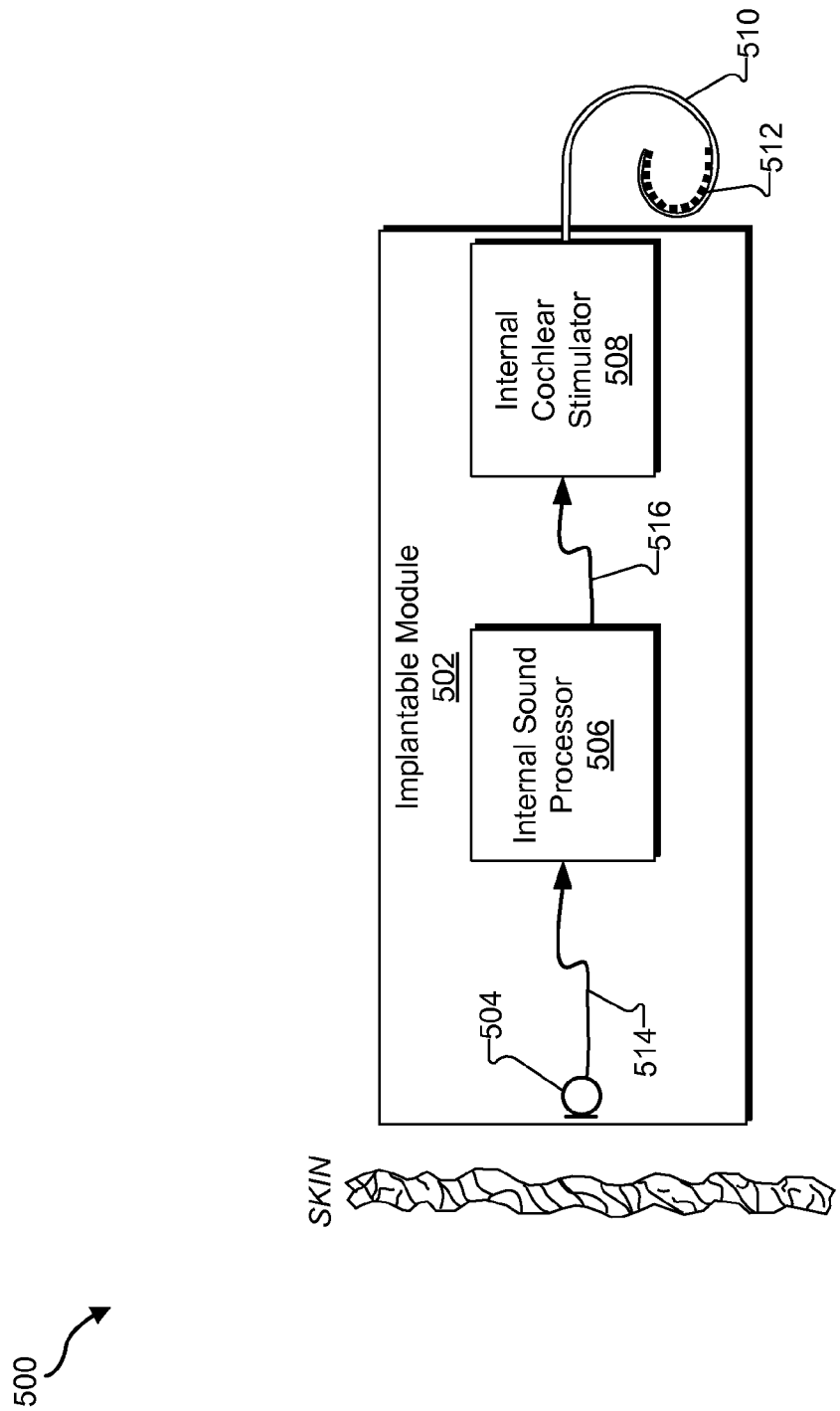
FIG. 5 illustrates an exemplary implementation of the cochlear implant system of FIG. 1 according to principles described herein.

FIG. 5 illustrates an exemplary fully implantable implementation 500 of internal sound processing subsystem 102 and stimulation subsystem 104. As shown in FIG. 5, fully implantable implementation 500 may include an implantable module 502 implanted internally within a patient. For example, implantable module 502 may be implanted with the head of a patient so that the implanted components of implantable module 502 are not visible to an external viewer. Implantable module 502 may include an internal microphone 504, an internal sound processor 506, and an internal cochlear stimulator ("ICS") 508. As shown in FIG. 5, a lead 510 having a plurality of electrodes 512 disposed thereon may be coupled to internal cochlear stimulator 508. Additional or alternative components may be included within fully implantable implementation 500 as may serve a particular application.

The facilities described in connection with FIGS. 3-4 may be implemented by or within one or more components shown within FIG. 5. For example, detection facility 302 may be implemented by internal microphone 504. Pre-processing facility 304, spectral analysis facility 306, noise reduction facility 308, mapping facility 310, stimulation strategy facility 312, communication facility 314, and/or storage facility 316 may be implemented by internal sound processor 506. Communication facility 402, current generation facility 404, and storage facility 408 may be implemented by internal cochlear stimulator 508. Stimulation facility 406 may be implemented by lead 510 and electrodes 512. As shown in FIG. 5, internal microphone 504 and internal sound processor 506 may be utilized without any components located external to the cochlear implant patient. As will be described in greater detail below, implantable module 502 may also be optionally utilized in conjunction with various external components.

Internal microphone 504 may detect an audio signal and convert the detected signal to a corresponding electrical signal. Internal microphone 504 may be implanted subcutaneously within the cochlear implant patient at any suitable location as may serve a particular application. The electrical signal may be sent from internal microphone 504 to internal sound processor 506 via a communication link 514, which may include a wire and/or any other suitable communication link.

Internal sound processor 506 is configured to process the converted audio signal to generate appropriate stimulation parameters for controlling internal cochlear stimulator 508. Exemplary components of internal sound processor 506 will be described in more detail below.

Internal sound processor 506 may be configured to transmit data (e.g., data representative of one or more stimulation parameters) to internal cochlear stimulator 508 via a communication link 516, which may include a wire and/or any other suitable communication link. It will be understood that communication link 516 may include a bi-directional communication link and/or one or more dedicated uni-directional communication links.

Internal cochlear stimulator 508 may be configured to generate electrical stimulation representative of an audio signal detected by internal microphone 504 in accordance with one or more stimulation parameters transmitted thereto by internal sound processor 506. Internal cochlear stimulator 508 may be further configured to apply the electrical stimulation to one or stimulation sites within the cochlea via one or more electrodes 512 disposed along lead 510.

To facilitate application of the electrical stimulation generated by internal cochlear stimulator 508, lead 510 may be inserted within a duct of the cochlea such that electrodes 512 are in communication with one or more stimulation sites within the cochlea. As used herein, the term "in communication with" refers to electrodes 512 being adjacent to, in the general vicinity of, in close proximity to, directly next to, or directly on the stimulation site. Any number of electrodes 512 (e.g., sixteen) may be disposed on lead 510 as may serve a particular application.

Figure 6:
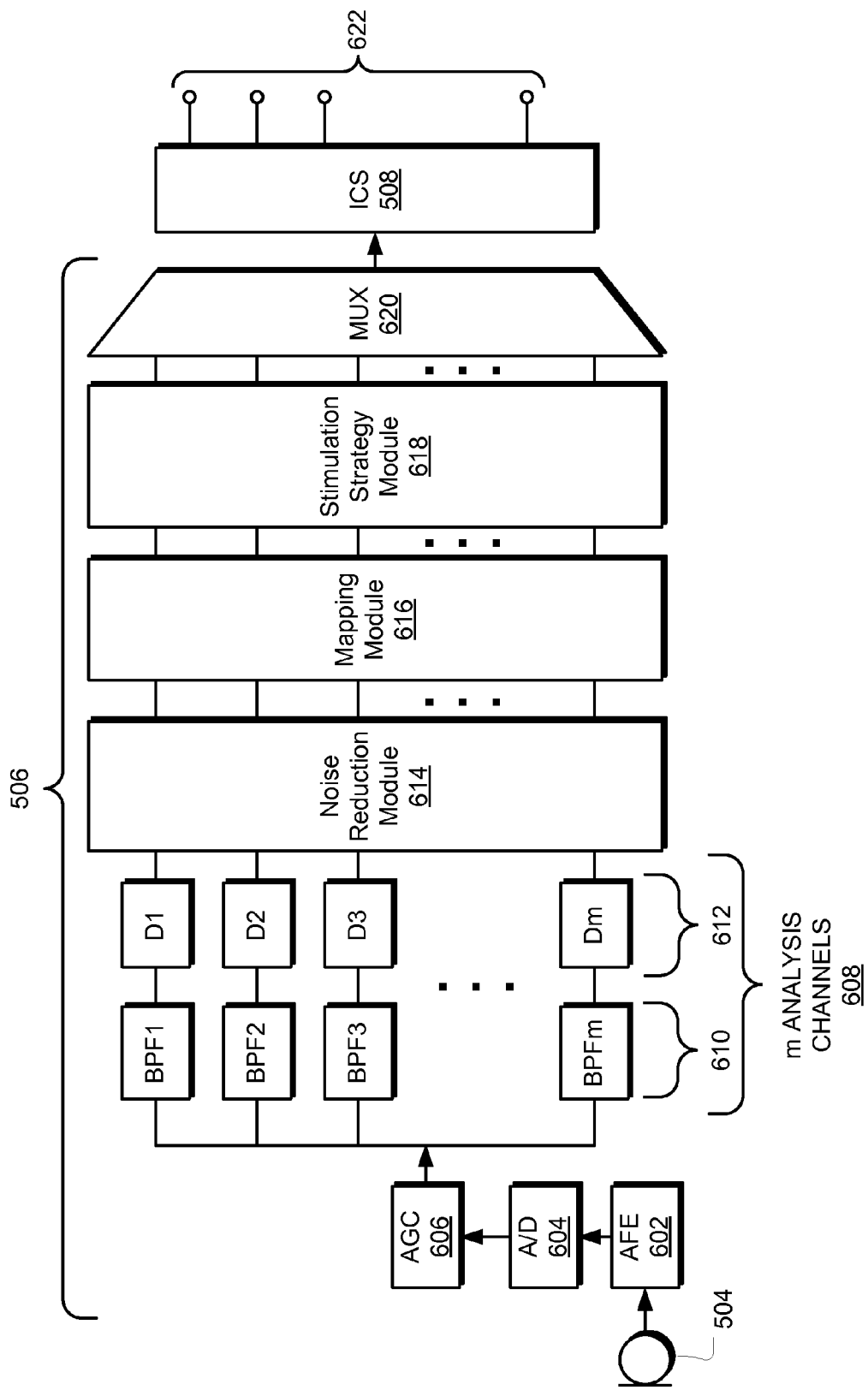
FIG. 6 illustrates components of an exemplary internal sound processor and an exemplary internal cochlear stimulator according to principles described herein.

FIG. 6 illustrates exemplary components of internal sound processor 506 and internal cochlear stimulator 508. The components shown in FIG. 6 may be configured to perform one or more of the processes associated with one or more of the facilities 302-316 associated with internal sound processing subsystem 102 and are merely representative of the many different components that may be included within internal sound processor 506.

As shown in FIG. 6, internal microphone 504 senses an audio signal, such as speech or music, and converts the audio signal into one or more electrical signals. These signals are then amplified in audio front-end ("AFE") circuitry 602. The amplified audio signal is then converted to a digital signal by an analog-to-digital ("A/D") converter 604. The resulting digital signal is then subjected to automatic gain control using a suitable automatic gain control ("AGC") unit 606.

After appropriate automatic gain control, the digital signal is subjected to a plurality of filters 610 (e.g., a plurality of band-pass filters). Filters 610 are configured to divide the digital signal into m analysis channels 608 each containing a signal representative of a distinct frequency portion of the audio signal sensed by microphone 502. Additional or alternative components may be used to divide the signal into the analysis channels 608 as may serve a particular application. For example, as described previously, one or more components may be included within sound processor 504 that are configured to apply a Discrete Fourier Transform to the audio signal and then divide the resulting frequency bins into the analysis channels 608.

As shown in FIG. 6, the signals within each analysis channel 608 may be input into an energy detector 612. Each energy detector 612 may include any combination of circuitry configured to detect an amount of energy contained within each of the signals within the analysis channels 608. For example, each energy detector 612 may include a rectification circuit followed by an integrator circuit.

After energy detection, the signals within the m analysis channels 608 are input into a noise reduction module 614. Noise reduction module 614 may perform one or more of the functions described in connection with noise reduction facility 308. For example, noise reduction module 614 may be configured to filter out acoustic content within the audio signal in accordance with one or more filtering parameters. In some examples, noise reduction module 614 may be configured to at least partially remove undesired audio content from one or more of the analysis channels 608, such as bodily noises picked up by internal microphone 504.

In some alternative examples, internal sound processor 506 may be configured so that an electrical or digital signal representative of an audio signal is processed by a noise reduction module 614 prior to being processed by the plurality of filters 610. For example, noise reduction module 614 may include a high-pass filter configured to at least partially remove at least a portion of an electrical signal that is representative of frequencies below a predetermined frequency threshold. Noise reduction module 614 will be described in more detail below.

Mapping module 616 may perform one or more of the functions described in connection with mapping facility 310. For example, mapping module 616 may map the signals in the analysis channels 608 to one or more stimulation channels after the signals have been subjected to noise reduction heuristics by noise reduction module 614. For example, signal levels of the noise reduced signals generated by noise reduction module 614 are mapped to amplitude values used to define the electrical stimulation pulses that are applied to the patient by internal cochlear stimulator 508 via M stimulation channels 622. In some examples, groups of one or more electrodes 512 may make up the M stimulation channels 622.

Stimulation strategy module 618 may perform one or more of the functions described in connection with stimulation strategy facility 312. For example, stimulation strategy module 618 may generate one or more stimulation parameters by selecting a particular stimulation configuration in which internal cochlear stimulator 710 operates to generate and apply electrical stimulation representative of various spectral components of an audio signal.

Multiplexer 620 may be configured to serialize the mapped signals so that they can be transmitted to internal cochlear stimulator 508. The internal cochlear stimulator 508 may then generate and apply electrical stimulation via one or more of the M stimulation channels 622 to one or more stimulation sites within the duct of the patient's cochlea in accordance with the one or more stimulation parameters.

As mentioned, there are number of limitations associated with a fully implantable cochlear implant system, such as fully implantable configuration 500. For example, internal microphone 504 may detect bodily noises that may interfere with the quality of the patient's listening experience. Additionally, one or more components within implantable module 502 (e.g., internal sound processor 506) may become degraded or damaged during use. Hence, the systems and methods described herein provide for one or more external components to be selectively used in conjunction with implantable module 502 in order to enhance the listening experiencing of the cochlear implant patient.

Figure 7:
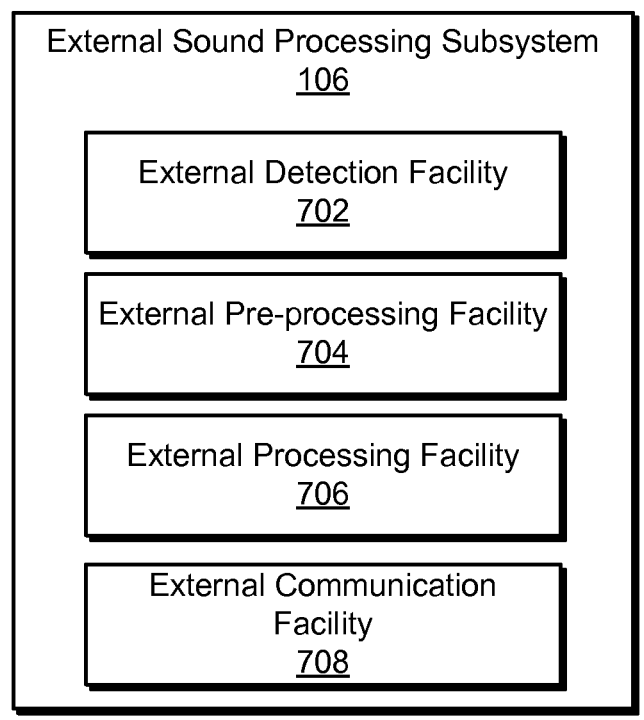
FIG. 7 illustrates exemplary components of an external sound processing subsystem according to principles described herein.

FIG. 7 illustrates exemplary components of external sound processing subsystem 106. External sound processing subsystem 106 may be selectively utilized by a cochlear implant patient in conjunction with internal sound processing subsystem 102 as described above. As shown in FIG. 7, external sound processing subsystem 106 may include an external detection facility 702, an external pre-processing facility 704, an external processing facility 706, and an external communication facility 708, which may be in communication with one another using any suitable communication technologies. Each of these facilities 702-708 may include any combination of hardware, software, and/or firmware as may serve a particular application. For example, one or more of facilities 702-708 may include a computing device or processor configured to perform one or more of the functions described herein. Facilities 702-708 will now be described in more detail.

External detection facility 702 may be configured to detect or sense one or more input audio signals presented to the patient. To this end, external detection facility 702 may include a microphone or other transducer. In some examples, the one or more audio signals may include speech. The one or more audio signals may additionally or alternatively include music, ambient noise, and/or other sounds.

External pre-processing facility 704 may be configured to perform various pre-processing operations on the one or more input audio signals detected by external detection facility 702. For example, external pre-processing facility 704 may amplify a detected audio signal, convert the audio signal to a digital signal, filter the digital signal with a pre-emphasis filter, subject the digital signal to automatic gain control, and/or perform one or more other signal processing operations on the detected audio signal.

External processing facility 706 may be configured to modify one or more characteristics of the input audio signal. For example, external processing facility 706 may be configured to frequency transpose or shift at least a portion of the frequency content in the input audio signal. In some examples, frequency content in the input audio signal may be frequency transposed to a higher frequency range.

External processing facility 706 may additionally or alternatively be configured to increase the amplitude of at least a portion of the frequency content in the input audio signal. For example, external processing facility 706 may include an amplifier configured to increase the amplitude and sound level of the input audio signal.

External communication facility 708 may be configured to facilitate communication between external sound processing subsystem 106 and internal sound processing subsystem 102. For example, external communication facility 708 may be configured to acoustically transmit an audio signal representative of the input audio signal to internal sound processing subsystem 102.

It will be recognized that one or more functions associated with external pre-processing facility 704 and external processing facility 706 may not be performed. For example, in some instances, external sound processing subsystem 106 may be configured to only amplify an input audio signal and generate an audio signal representative of the amplified audio signal for acoustic transmission to internal sound processing subsystem 102.

Figure 8:
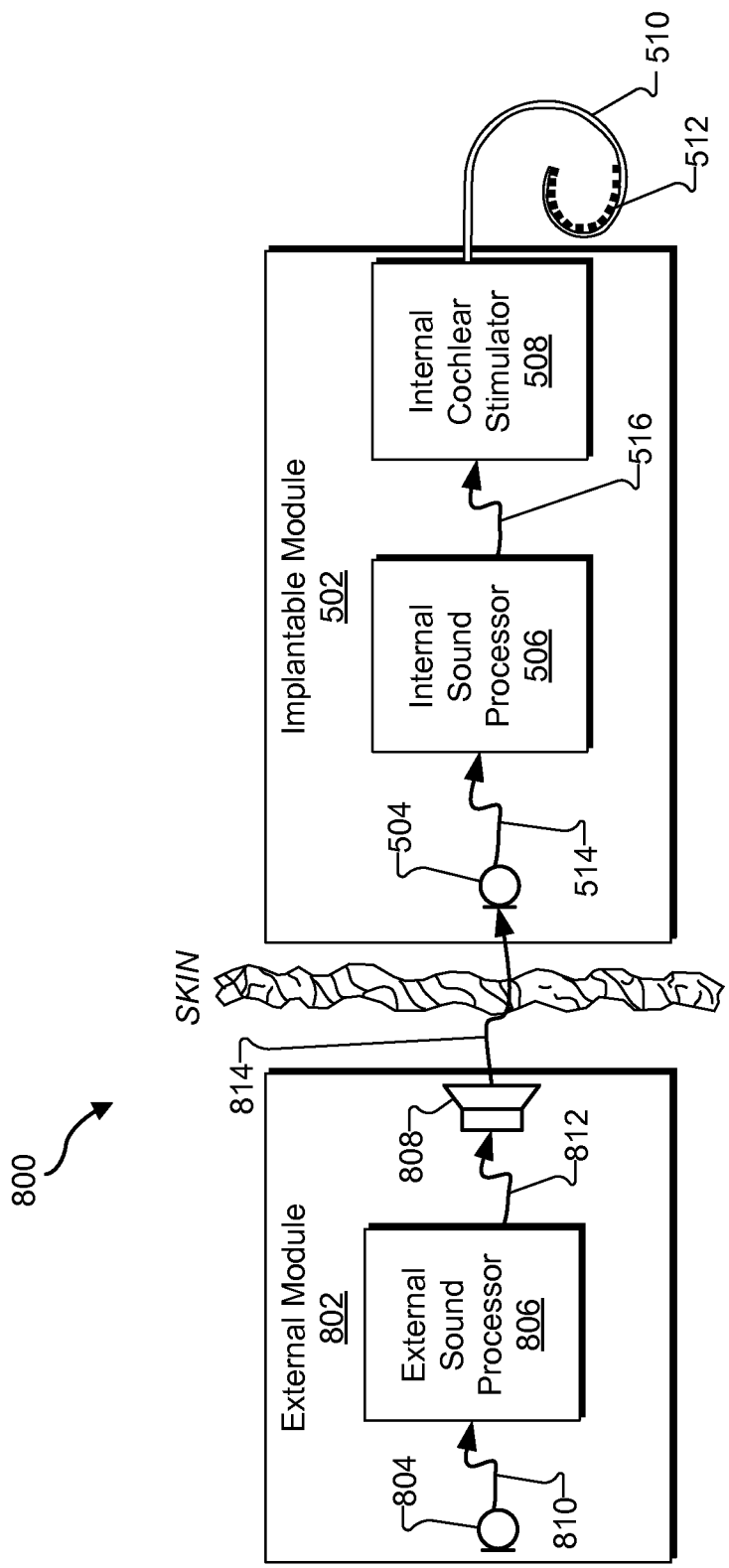
FIG. 8 illustrates an exemplary implementation of the cochlear implant system of FIG. 1 according to principles described herein.

FIG. 8 illustrates an exemplary implementation 800 of cochlear implant system 100 wherein an external module 802 may be selectively used by a patient in combination with the implantable module 502 described in connection with FIG. 5. As shown in FIG. 8, external module 802 may include an external microphone 804, an external sound processor 806, and an external speaker 808. Additional or alternative components may be included within implementation 800 as may serve a particular application.

The facilities described in connection with FIG. 7 may be implemented by or within one or more components shown within FIG. 8. For example, external detection facility 702 may be implemented by external microphone 804. External pre-processing facility 704 and external processing facility 706 may be implemented by external sound processor 806. External communication facility 708 may be implemented by external speaker 808.

As illustrated in FIG. 8, external module 802 may be located external to a cochlear implant patient. For example, external module 802 may comprise a headpiece mounted on a patient's head near at least a portion of implantable module 502. External module 802 may be mounted on an exterior of a patient in any suitable manner. For example, external module 802 may comprise an external magnet corresponding to an internal magnet included on implantable module 502. The external magnet may securely hold an external module 802 on a patient's head so that external module 802 is positioned near at least a portion of implantable module 502.

External microphone 804 may detect an input audio signal (e.g., an audio signal presented to or otherwise intended for a cochlear implant patient) and convert the detected signal to a corresponding electrical signal. External microphone 804 may be placed external to the patient, at the entrance to the ear canal of the patient, or at any other suitable location as may serve a particular application. The electrical signal may be sent from external microphone 804 to external sound processor 806 via a communication link 810, which may include a telemetry link, a wire, and/or any other suitable communication link.

In some examples, external microphone 804 may include an array of microphones configured to detect the input signal. The array of microphones may be positioned at any suitable location. However, for illustrative purposes, it will be assumed in the examples given herein that external microphone 804 includes a single microphone.

External sound processor 806 is configured to process the converted input audio signal in accordance with one or more signal processing heuristics. For example, external sound processor 806 may be configured to generate an amplified representation of the input audio signal that may be transmitted by external module 802 to implantable module 502. External sound processor 806 may additionally or alternatively be configured to produce a frequency transposed representation of the input audio signal detected by external microphone 804. External sound processor 806 may include or be implemented within a headpiece, a behind-the-ear ("BTE") unit, a portable speech processor ("PSP"), and/or any other sound processing unit as may serve a particular application.

External sound processor 806 may be further configured to transmit an electrical signal representative of the processed input audio signal to external speaker 808 via a communication link 812, which may include a wire and/or any other suitable communication link. In some examples, external speaker 808 may be configured to convert the electrical signal received from external sound processor 806 into an audio signal representative of the input audio signal. For example, external speaker 808 may include an electromechanical transducer configured to convert the electrical signal into an audio signal that is transcutaneously transmitted by external speaker 808 to internal microphone 504 of implantable module 502 via acoustic communication link 814.

Figure 9:
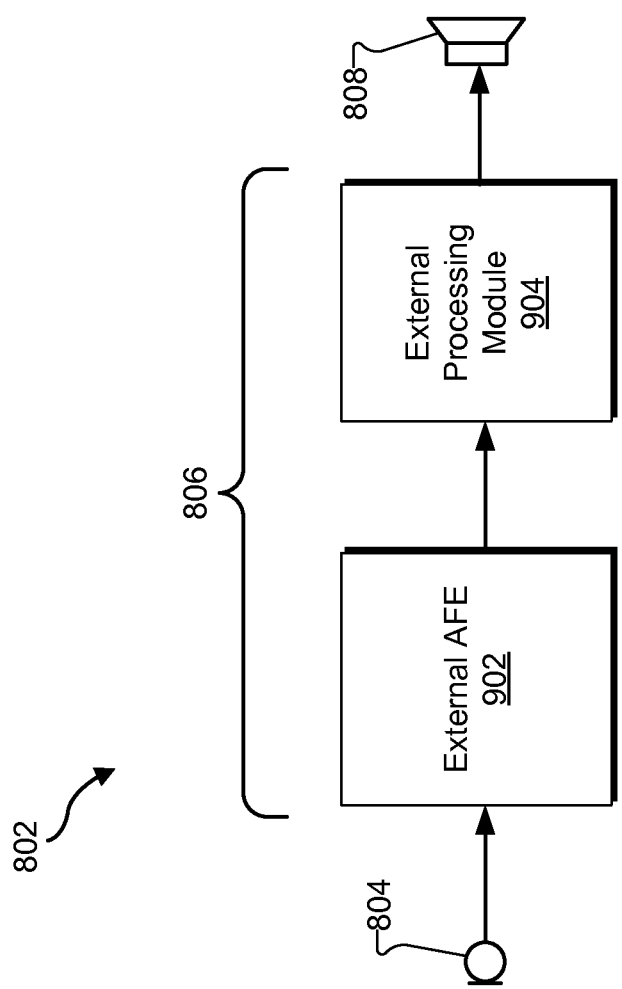
FIG. 9 illustrates exemplary components that may be included within an external module of a cochlear implant system according to principles described herein.

FIG. 9 illustrates components of an exemplary external sound processor 806 coupled to an external microphone 804 and an external speaker 808. The components shown in FIG. 9 may be configured to perform one or more of the processes associated with one or more of the facilities 702-708 associated with external sound processing subsystem 106 and are merely representative of the many different components that may be included within external sound processor 806.

As shown in FIG. 9, external microphone 804 senses an audio signal, such as speech or music, and converts the audio signal into one or more electrical signals. These signals are then amplified in external AFE circuitry 902. In some examples, the amplified audio signal may be converted to a digital signal by an analog-to-digital converter and/or subjected to automatic gain control using an automatic gain control unit. The analog and/or digital electrical signals may then be processed by external processing module 904. External processing module 904 may be configured to modify one or more characteristics of the input audio signal, such as the frequency and/or amplitude of the input audio signal, in accordance with one or more sound processing heuristics.

For example, external processing module 904 may be configured to transpose the frequency content of an input audio signal from a first frequency range to a second frequency range. The second frequency range may be higher than the first frequency range so that internal sound processor 506 may be able to distinguish between the input audio signal and other signals (e.g., bodily noise) detected by internal microphone 504.

Figure 10:
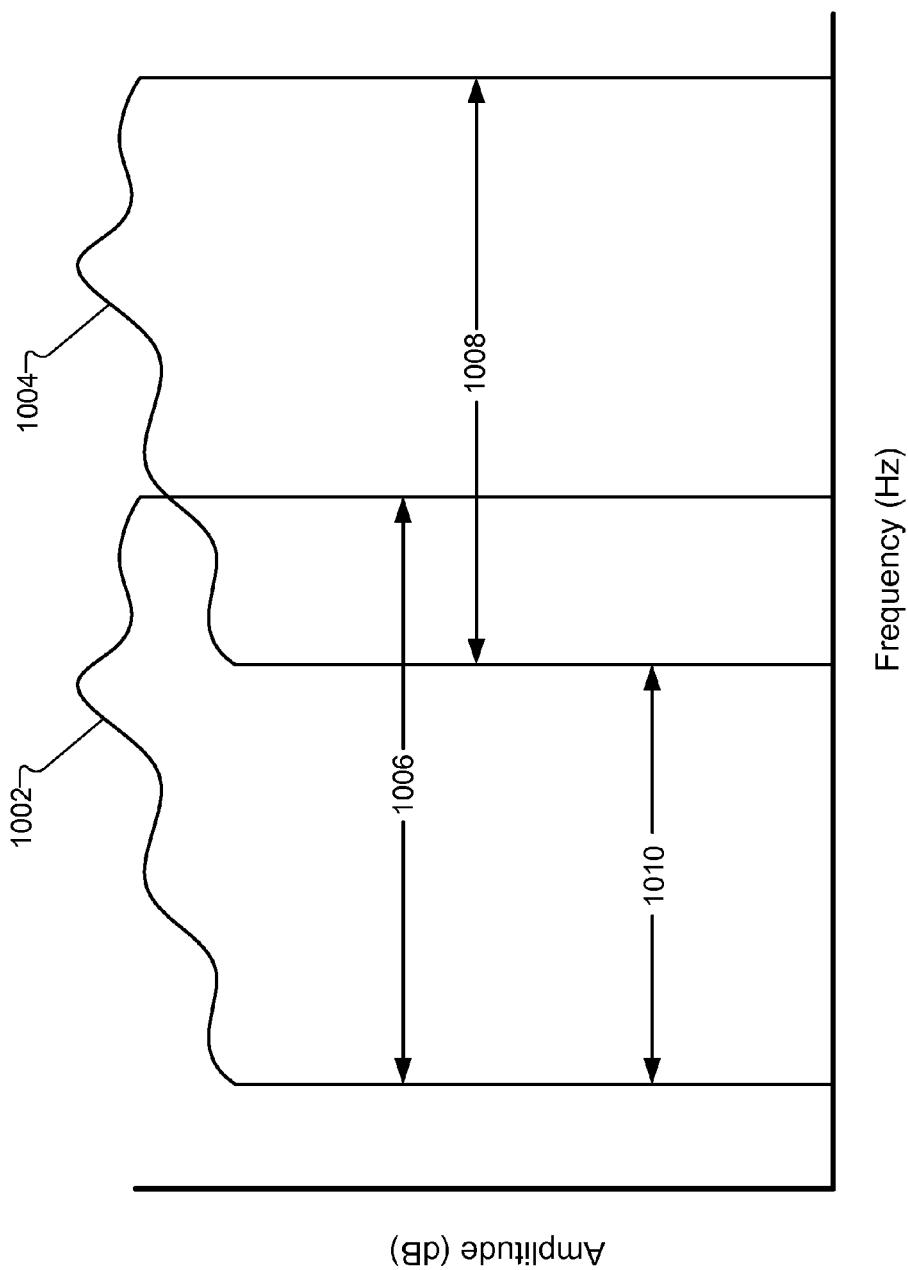
FIG. 10 illustrates an exemplary implementation of a frequency transposing strategy according to principles described herein.

To illustrate, FIG. 10 shows exemplary frequency content 1002 included within an input audio signal detected by external microphone 804 and exemplary frequency content 1004 of a transposed representation of the input audio signal. As shown in FIG. 10, frequency content 1002 may be included within a first frequency range 1006 and frequency content 1004 may be included within a second frequency range 1008 that is higher than the first frequency range 1006.

In some examples, the frequency transposed representation of the input audio signal (i.e., frequency content 1004) may be transmitted by external speaker 808 to internal microphone 504. In this manner, internal sound processor 506 may be able to distinguish between frequency content corresponding to the input signal and frequency content corresponding to other audio signals detected by internal microphone 504. For example, internal microphone 504 may concurrently detect an audio signal representative of bodily noise and the audio signal acoustically transmitted by speaker 808. The bodily noise may include frequency content in a relatively low frequency range (e.g., frequency range 1010).

Noise reduction module 614 within internal sound processor 506 may remove at least a portion of the other audio content, such as bodily noises, detected by internal microphone 504 by at least partially filtering out or not processing acoustic content within frequency range 1010. Accordingly, other acoustic content, such as bodily noises, may be at least partially removed by noise reduction module 614, while the audio signal transmitted by external speaker 808, such as acoustic content within transposed frequency range 1008, may be passed-on by noise reduction facility 308 to be further processed by internal sound processor 506.

Noise reduction module 614 may use any suitable technique for filtering and/or otherwise processing acoustic content detected by internal microphone 504. In some examples, noise reduction module 614 may process the acoustic content using a high-pass filter and/or one or more band-pass filters to reduce and/or eliminate acoustic content included within certain predetermined frequency ranges, such as bodily noises within frequency range 1010. For example, band-pass filters 610 may be configured to process only acoustic content within frequency ranges above frequency range 1010. In additional examples, noise reduction module 614 may include a high-pass filter that may filter acoustic content prior to or following processing by band-pass filters 610. The high-pass filter may at least partially filter out electrical signals representative of acoustic content below a predetermined threshold frequency, allowing electrical signals representative of the acoustic content above the predetermined frequency to pass. In some examples, noise reduction module 614 may be configured to simply not process acoustic content below the predetermined threshold frequency.

The transposed audio signal may be processed by internal sound processor 506 in a manner that allows the patient to perceive the transposed audio signal in substantially the same frequency range as the input audio signal. For example, internal sound processor 506 may be configured to transpose the transposed audio signal back to the input frequency range associated with the input audio signal prior to generating stimulation parameters representative of the input audio signal.

In some examples, internal sound processor 506 may be configured to account for the frequency transposition by adjusting a manner in which the frequencies included within the transposed audio signal are mapped to electrodes 512. In this manner, internal sound processor 506 may not have to transpose the acoustically transmitted audio signal back to an input frequency range associated with the input audio signal.

Figure 11:
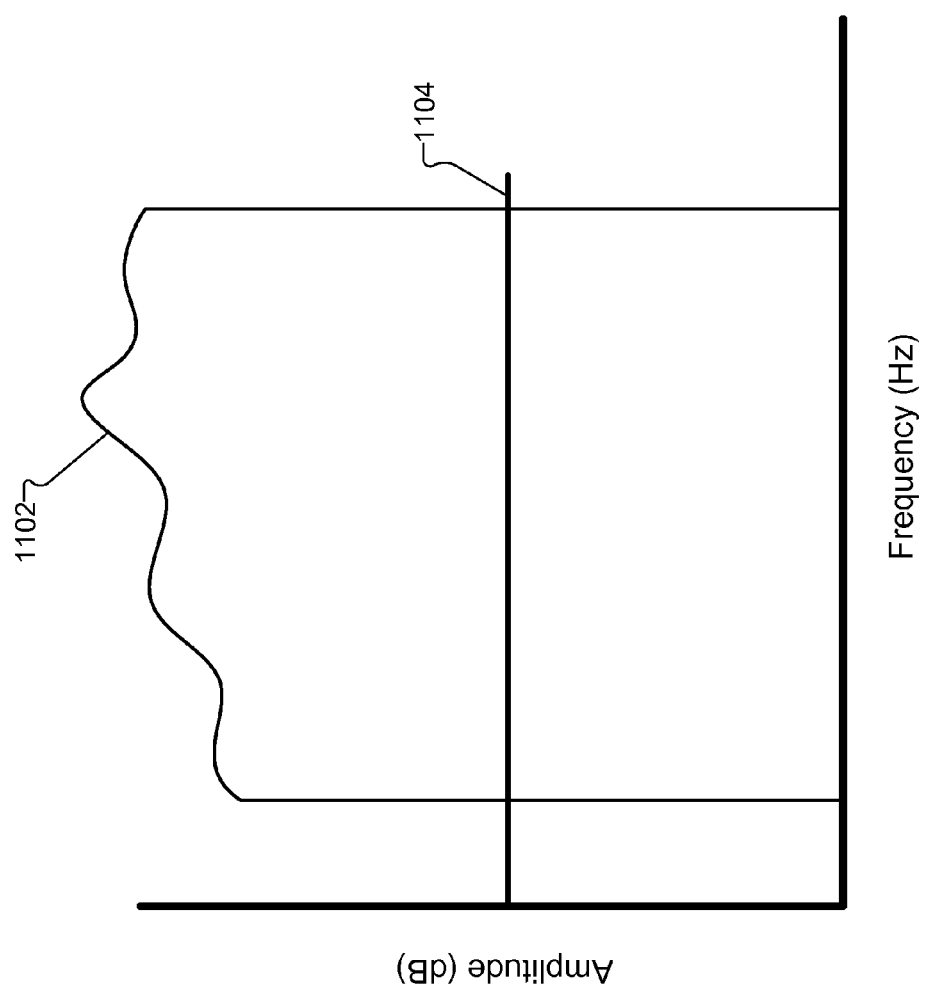
FIG. 11 shows illustrates an exemplary implementation of an audio signal amplitude modification strategy.

Internal sound processor 506 may additionally or alternatively be configured to at least partially remove acoustic content not corresponding to an audio signal acoustically transmitted by external module 802 by processing only acoustic content having an amplitude greater than a predetermined threshold amplitude. For example, FIG. 11 illustrates an exemplary implementation of an audio signal amplitude modification strategy that may be used to facilitate processing of an audio signal acoustically transmitted by external module 802. In some examples, external module 802 may be configured to amplify an input audio signal and transmit an amplified representation of the audio signal to internal sound processor 506 for further processing. FIG. 11 shows acoustic content 1102 corresponding to an amplified input audio signal. As illustrated in FIG. 11, the amplified representation of the input audio signal may have amplitudes above a predetermined threshold amplitude 1104.

The amplified representation of the input audio signal may be transmitted by external speaker 808 to internal microphone 504. Internal sound processor 506 may be configured to filter out acoustic content having amplitudes lower than predetermined threshold amplitude 1104. Accordingly, bodily noises and other acoustic content having an amplitude below threshold amplitude 1104 may be at least partially removed from the audio signal, while audio content above threshold amplitude 1104, such as acoustic content 1102, may be processed by internal sound processor 506.

In some examples, external module 802 may be selectively removed from being communicatively couple to internal module 502 and/or otherwise disabled. In such instances, internal module 502 may be configured to automatically perform portions of the signal detection and/or the signal processing heuristics that the external module 802 had been performing prior to being disabled. In this manner, external module 802 may be selectively used by a patient when the patient desires increased signal processing capabilities.

Figure 12:
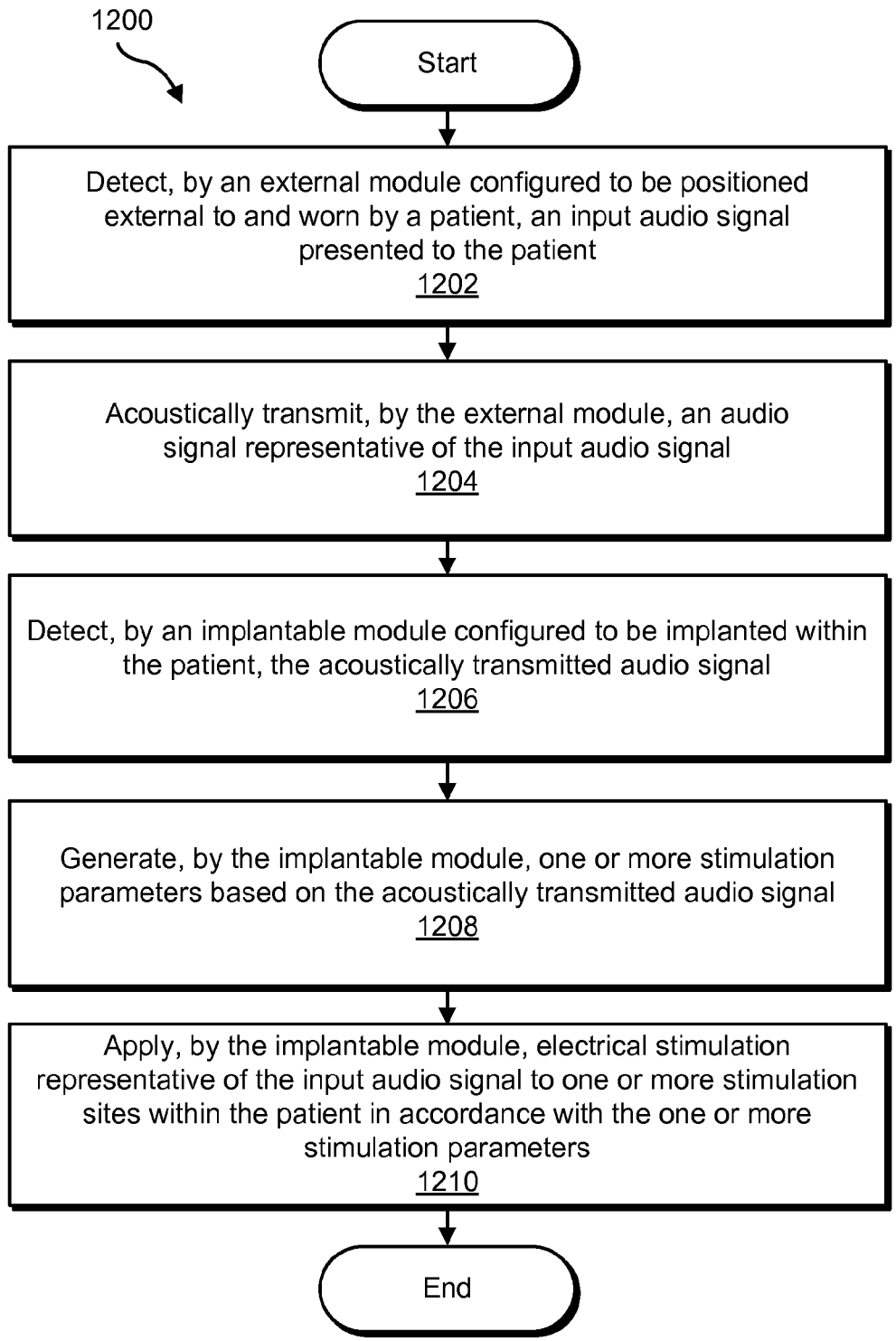
FIG. 12 illustrates an exemplary method for using a cochlear implant system according to principles described herein.

FIG. 12 illustrates an exemplary method 1200 of using a fully implantable cochlear implant system including optional external components. While FIG. 12 illustrates exemplary steps according to one embodiment, other embodiments may omit, add to, reorder, and/or modify any of the steps shown in FIG. 12. It will be recognized that any of the systems, subsystems, facilities, and/or modules may be configured to perform one or more of the steps shown in FIG. 12.

In step 1202, an external module that is configured to be positioned external to and worn by a patient may detect an input audio signal presented to the patient. Step 1202 may be performed by detection facility 702, for example, in any of the ways described herein.

In step 1204, the external module may acoustically transmit an audio signal representative of the input audio signal detected in step 1202. The audio signal representative of the input audio signal may be acoustically transmitted in any of the ways described herein. For example, the audio signal representative of the input audio signal may be acoustically transmitted by external speaker 808 of external module 802.

In step 1206, an implantable module configured to be implanted within the patient may detect the acoustically transmitted signal. For example, internal microphone 504 of implantable module 502 may detect the acoustic signal transmitted by external speaker 808. Step 1206 may be performed by detection facility 302, for example, in any of the ways described herein.

In step 1208, the implantable module may generate one or more stimulation parameters based on the acoustically transmitted audio signal. For example, the internal sound processor 506 of internal module 502 may generate one or more stimulation parameters.

In step 1210, the implantable module may apply electrical stimulation representative of the input audio signal to one or more stimulation sites within the patient in accordance with the one or more stimulation parameters. For example, stimulation facility 410 may apply electrical stimulation to the one or more stimulation sites.

As detailed above, the cochlear implant systems and methods described herein may result in an enhanced listening experience for the cochlear implant patient and may provide the patient with an option of utilizing external components in conjunction with fully implantable components. The cochlear implant systems and methods described herein may enable a cochlear implant patient to receive stimulation representing various sounds in the patient's environment using a fully implantable system alone. The cochlear implant systems and methods may also enable the patient to utilize external components (e.g., an externally worn headpiece) to enhance the quality of sounds detected by an implanted microphone and/or to compensate for various implanted components that are not functioning properly. Various heuristics applied to an audio signal detected by an implanted microphone may filter out noise in the audio signal, such as bodily noise, that may interfere with the patient's listening experience.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    detecting, by an external microphone included in an external module positioned external to and worn by a patient, an input audio signal presented to the patient;
    processing, by an external processing facility included in the external module, the input audio signal detected by the external microphone in accordance with one or more signal processing heuristics;
    transmitting, by the external processing facility included in the external module, an electric signal representative of the processed input audio signal;
    receiving, by an external speaker included in the external module, the processed input audio signal from the external processing facility;
    acoustically transmitting, by the external speaker included in the external module, an audio signal representative of the processed input audio signal;
    detecting, by an implantable module implanted within the patient, the acoustically transmitted audio signal representative of the processed input audio signal as transmitted by the external module;
    generating, by the implantable module, one or more stimulation parameters based on the acoustically transmitted audio signal; and
    applying, by the implantable module, electrical stimulation representative of the input audio signal to one or more stimulation sites within the patient in accordance with the one or more stimulation parameters.

2. The method of claim 1, further comprising at least partially removing, by the implantable module, other acoustic content detected by the external microphone.

3. The method of claim 2, wherein the at least partially removing the other acoustic content comprises at least one of filtering out the other acoustic content and not processing the other acoustic content.

4. The method of claim 2, wherein the at least partially removing the other acoustic content comprises processing only acoustic content having an amplitude greater than a predetermined threshold amplitude.

5. The method of claim 2, wherein the other acoustic content comprises bodily noises.

6. The method of claim 1, wherein the acoustically transmitted audio signal comprises a frequency transposed representation of the input audio signal.

7. The method of claim 6, further comprising transposing, by the implantable module, the acoustically transmitted audio signal back to an input frequency range associated with the input audio signal.

8. The method of claim 6, further comprising mapping, by the implantable module, frequencies included within the frequency transposed representation of the input audio signal to one or more electrodes without transposing the acoustically transmitted audio signal back to an input frequency range associated with the input audio signal.

9. The method of claim 6, wherein the frequency transposed representation of the input audio signal comprises frequency content in a frequency range that is higher than an input frequency range associated with the input audio signal.

10. A method comprising:
    concurrently detecting, by an internal microphone that is entirely implanted within a patient,
        a first audio signal representative of bodily noise that includes frequency content included in a first frequency range, and
        a second audio signal acoustically transmitted by a speaker externally worn by the patient, the audio signal comprising frequency content that is transposed from the first frequency range to a second frequency range that is higher than the first frequency range;
    processing, by an internal sound processor that is implanted within the patient, the first and second audio signals by
        filtering the first and second audio signals to filter out the frequency content included in the first frequency range, and
        using the transposed frequency content in the second frequency range to generate one or more stimulation parameters; and
    applying, by an internal cochlear stimulator that is implanted within the patient, electrical stimulation representative of the audio signal to one or more stimulation sites with the patient in accordance with the one or more stimulation parameters.

* * * * *